United States Patent
Sumetsky

(10) Patent No.: US 8,818,152 B2
(45) Date of Patent: Aug. 26, 2014

(54) MICROBUBBLE OPTICAL RESONATOR

(75) Inventor: Mikhail Sumetsky, Bridgewater, NJ (US)

(73) Assignee: OFS Fitel, LLC, Norcross, GA (US)

(*) Notice: Subject to any disclaimer, the term of this patent is extended or adjusted under 35 U.S.C. 154(b) by 179 days.

(21) Appl. No.: 13/618,434

(22) Filed: Sep. 14, 2012

(65) Prior Publication Data

US 2013/0219970 A1 Aug. 29, 2013

Related U.S. Application Data

(62) Division of application No. 12/658,090, filed on Feb. 2, 2010, now Pat. No. 8,515,227.

(60) Provisional application No. 61/159,822, filed on Mar. 13, 2009.

(51) Int. Cl.
  G02B 6/26 (2006.01)
  G02B 6/42 (2006.01)
  G02B 5/20 (2006.01)
  G02B 6/293 (2006.01)

(52) U.S. Cl.
  CPC .............. *G02B 5/20* (2013.01); *G02B 6/29335* (2013.01); *G02B 6/29341* (2013.01)
  USPC ............................................. 385/50; 385/32

(58) Field of Classification Search
  CPC .......................... G02B 6/29335; G02B 6/29341
  See application file for complete search history.

(56) References Cited

U.S. PATENT DOCUMENTS

| | | | | |
|---|---|---|---|---|
| 6,488,861 B2* | 12/2002 | Iltchenko et al. | ............... | 216/24 |
| 6,490,039 B2* | 12/2002 | Maleki et al. | ................. | 356/436 |
| 6,507,684 B2* | 1/2003 | Tapalian et al. | ................. | 385/30 |
| 6,668,111 B2* | 12/2003 | Tapalian et al. | ................. | 385/28 |
| 6,925,226 B2* | 8/2005 | Lim et al. | ......... | 385/32 |
| 7,535,634 B1* | 5/2009 | Savchenkov et al. | ......... | 359/346 |
| 7,570,850 B1* | 8/2009 | Matsko et al. | ................. | 385/30 |
| 7,702,202 B2* | 4/2010 | Koch et al. | ..................... | 385/50 |
| 8,515,227 B2* | 8/2013 | Sumetsky | ...................... | 385/50 |
| 2002/0018617 A1* | 2/2002 | Iltchenko et al. | ............... | 385/28 |
| 2003/0063426 A1* | 4/2003 | Smirnov et al. | ............... | 361/159 |
| 2003/0206693 A1* | 11/2003 | Tapalian et al. | ................. | 385/28 |
| 2004/0137478 A1* | 7/2004 | Arnold et al. | ..................... | 435/6 |
| 2006/0285799 A1* | 12/2006 | Spillane et al. | ................. | 385/50 |
| 2008/0265147 A1* | 10/2008 | Fan et al. | ................. | 250/227.24 |
| 2010/0231903 A1* | 9/2010 | Sumetsky | ..................... | 356/246 |
| 2013/0219970 A1* | 8/2013 | Sumetsky | ...................... | 65/406 |

* cited by examiner

*Primary Examiner* — Rhonda Peace
(74) *Attorney, Agent, or Firm* — Wendy W. Koba, Esq.

(57) ABSTRACT

An optical microresonator is configured as an optical microbubble formed along a section of an optical microcapillary. The curvature of the outer surface of the microbubble creates an optical resonator with a geometry that encourages the circulating WGMs to remain confined in the central region of the bubble, creating a high Q optical resonator. The resonator may be tuned by modifying the physical properties of the microbubble, allowing the resonator to be used as an optical filter. The resonator may also be used as a sensor or laser by introducing the material to be sensed (or the active laser material) into the microcapillary along which the microbubble is formed.

9 Claims, 2 Drawing Sheets

MICROBUBBLE OPTICAL RESONATOR

CROSS-REFERENCE TO RELATED APPLICATIONS

This application is a divisional of U.S. application Ser. No. 12/658,090, filed Feb. 2, 2010 now U.S. Pat. No. 8,515,227, which claims the benefit of U.S. Provisional Application No. 61/159,822, filed Mar. 13, 2009, both of which are herein incorporated by reference.

TECHNICAL FIELD

The present invention relates to an optical microresonator and, more particularly, to a microbubble-type optical resonator formed along a section of an optical microcapillary.

BACKGROUND OF THE INVENTION

Microcavity optical resonators are a basic element of many photonic circuits, including filters, sensors, lasers and the like. Ever-increasing demands for improvement in the operation of microcavity resonators are associated with parameters such as their Q-factor, tunability (filtering), robustness and efficiency. Particularly important realizations of the optical microcavity are the "microsphere" and "microtoroid". An optical microsphere is used to form an optical whispering-gallery-mode (WGM) resonator that supports a special set of resonator modes. These resonator modes represent optical fields confined to an interior region of the microsphere, propagating around the "equator" of the sphere in association with the total internal reflection at the boundary of the sphere. Microspheres with diameters on the order of 10-100 microns have been used to form compact optical resonators. Since these resonators exhibit dimensions much larger than the wavelength of an associated optical signal, the optical loss associated with the finite curvature of the resonator is generally very small. The primary sources of optical loss include optical absorption in the material of the sphere and optical scattering due to the homogeneity of the sphere (e.g., irregularities on the surface of the sphere), both of which can be controlled by the fabrication process. As a result, a relatively high Q-factor can be achieved with an optical microsphere, allowing for the microsphere to find use as a highly accurate optical sensor or laser.

However, in applications where the microsphere is used as an optical sensor, the material being "sensed" needs to be placed in close proximity to the sphere. In some conventional arrangements, the material is contained with an optical microfiber probe which must be positioned at the surface of the microsphere, which is both awkward and difficult to maintain and control on a repeated basis.

Additionally, optical microspheres are difficult to use as a filtering element, since they are relatively rigid in structure and difficult to "tune" to adjust the wavelength(s) passed/blocked by the microsphere device. Another problem, which is characteristic for the microsphere optical cavity, is the very dense and practically chaotic distribution of its resonant frequencies, making the microsphere difficult to use in filtering applications.

Recently, an optical microcapillary has been demonstrated as a microfluidic optical sensor that overcomes some of the above-mentioned microsphere problems. An exemplary prior art liquid-core optical ring resonator sensor (LCORRS) 1 is shown in FIG. 1. LCORRS 1 comprises a silica capillary 2 coupled to a waist area 3 of an optical fiber taper 4. An optical signal is coupled into optical fiber taper 4 and propagates therealong (the direction of the propagating optical shown by the arrows in FIG. 1). As the propagating signal reaches waist area 3, a portion of the signal will be evanescently coupled into capillary 2 and begin to circulate as whispering gallery modes (WGMs) inside the capillary wall. This coupling is the result of the relatively thin dimension (on the order of a few microns) of the capillary wall.

In use as a sensor, a liquid or gas being tested is introduced to optical microcapillary 2, as shown in FIG. 1, where the WGMs of the probing optical signal will interact with the sample and, as a result, modify the optical signal propagating along optical fiber taper 4. An analysis of the optical signal exiting optical fiber taper 4 can then be used to define the characteristics of the sample being tested. An LCORRS has also been demonstrated as a laser, by utilizing an active optical fluid passing through microcapillary 2.

The ability to pass the sensing/lasing material through a microcapillary and provide optical sensing/lasing with an adjacent microfiber taper results in an optical sensor that is more convenient to use than the above-described microsphere and microtoroid. In particular, the sample liquid is situated inside the capillary and the liquid flow does not perturb the coupling between the microfiber and the capillary. Moreover, the capillary-microfiber assembly can be "fixed" within a low-index polymer matrix, forming a device that is extremely robust and convenient for many applications.

However, problems remain with the sensitivity that may be achieved with an LCORRS device. That is, since the microcapillary is not "bounded", the circulating WGMs will tend to spread outwards along the length of the microcapillary (shown by the arrows within the microcapillary 2 of LCORRS 1). Thus, the localized eigenmodes of the circulating WGMs do not remain confined to waist region W and, therefore, the Q-factor of the device is rather limited. In other words, the light launched into the LCORRS device cannot dwell is the waist area for a long time and escapes in both directions along the capillary axis. As discussed above, an important feature of "sensing" optical signals is creating and maintaining a "high Q", allowing for the sensing process to exhibit extremely high levels of sensitivity.

Thus, a tension remains between these two types of prior art sensors, where the microsphere/microtoroid has the advantage of desirable high Q-factor, but is not robust or practical in implementation, while the LCORRS sensor is very robust and applicable in many situations, but has limits on the Q-factor that may be achieved.

Thus, a need remains in the art for a microresonator that is capable of achieving the high Q-factor associated with the microsphere, yet is practical and robust in implementation.

SUMMARY OF THE INVENTION

The needs remaining in the prior art are addressed by the present invention, which relates to an optical microresonator and, more particularly, to a microbubble-type optical resonator formed along a section of an optical microcapillary.

In accordance with the present invention, a micro "bubble" is formed along an optical microcapillary, the microcapillary taking the form of a tube. The "bubble" comprises a curved film of optically transparent material that can be created while the microcapillary is still in its malleable form. The curvature creates an optical resonator with a geometry that encourages the circulating WGMs to remain confined in the central region of the bubble, preventing the wandering associated with the microcapillary-based prior art LCORRS devices. By confining the propagating signal in this fashion, fewer modes will be supported and provide the wavelength separation required for filtering applications. The geometry of the bubble itself is not necessarily spherical, but may exhibit an elongated or 'squeezed' bubble profile. Indeed, one or more separate bubbles, or one or more "curves" on the outer surface of the microcapillary tube have been found sufficient to confine the circulating WGMs in a manner which forms a high Q resonator.

The microbubble optical resonator of the present invention may be used as a filter, sensor or laser, with a material to be sensed (liquid, gas, solid) or active laser material (liquid, gas or solid) injected along the microcapillary within which the microbubble is formed. An optical signal is coupled into the microbubble via an associated optical waveguide, prism, grating, tapered fiber or other suitable coupling device. A coupling tapered fiber may take the form of an optical microfiber including a tapered region formed to contact the surface of the microbubble and provide high coupling efficiency between the fiber and the microbubble. The thickness of the curved film of the microbubble's outer surface is also a factor in determining the coupling efficiency between the optical coupling path (waveguide, prism, fiber) and the microbubble resonator.

The use of a microbubble formed along a section of optical microcapillary allows for the sensor to retain the preferable qualities of the prior art LCORRS devices in terms of robustness and ease of use. That is, the sample being tested (or the amplifying medium) will still pass along the microcapillary/bubble structure and remain physically isolated from the optical fiber (or prism, grating, waveguide, etc.) supporting the propagating optical signal used in various applications.

The microbubble resonator of the present invention may be disposed within and encapsulated by a polymer matrix material having a relatively low index of refraction. The encapsulation functions to improve the rigidity and stability of the device. In this embodiment, an etchant may be used to remove the microcapillary material in the region of the microbubble, forming a cavity within the encapsulant that functions as the microbubble resonator.

Tuning of the microbubble resonator for filtering applications may be performed by introducing physical changes to the microbubble. These physical changes include, but are not limited to, mechanical deformation to the bubble geometry, temperature variation of the bubble and application of electromagnetic radiation to the bubble.

Other and further advantages and aspects of the present invention will become apparent during the course of the following discussion and by reference to the accompanying drawings.

BRIEF DESCRIPTION OF THE DRAWINGS

Referring now to the drawings.

DETAILED DESCRIPTION

Figure 1:
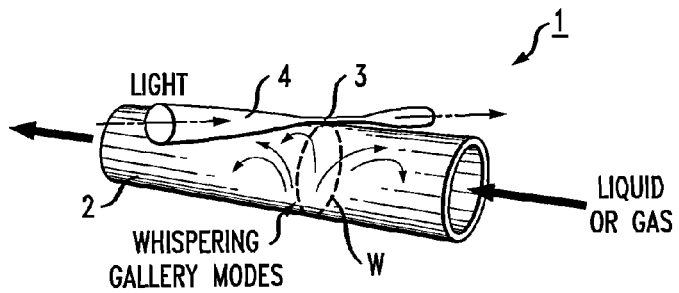
FIG. 1 illustrates a prior art liquid-core optical ring resonator sensor (LCORRS)
Figure 2:
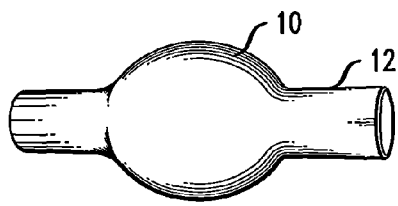
FIG. 2 illustrates an exemplary microbubble optical resonator formed in accordance with the present invention, the microbubble resonator of this embodiment formed along an optical microcapillary.
Figure 3:
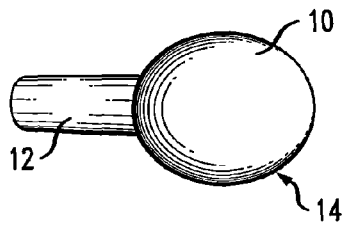
FIG. 3 shows an alternative embodiment of the present invention in the form of an optical microbubble resonator formed at a terminal portion of an optical microcapillary.

FIG. 2 illustrates an exemplary microbubble 10 formed along a section of optical microcapillary 12 in accordance with the principles of the present invention. As shown, the "bubble" takes the form of a curved film of optically transparent material, in this case the material used to form microcapillary 12 itself. Various methods may be used to create microbubble 10, where an exemplary method utilizes local melting of a section of microcapillary 12 while under pressure. FIG. 3 illustrates an alternative arrangement, with a microbubble 10 formed at a terminal portion 14 of microcapillary 12. In either configuration, it is to be understood that the microbubble need not be 'spherical' in form, and may take the shape of an elongated or squeezed bubble. One or more such microbubbles may be formed along a section of microcapillary and the bubble(s) may dominate the entire extent of the microcapillary, or only a portion thereof.

Optical microbubble resonator 10 as shown in FIG. 2 may be used as part of an optical filter (a tunable, wavelength selective device), an optical sensor or an optical laser. When used as an optical sensor, a propagating optical signal is evanescently coupled into the microbubble to create circulating WGMs around the equator of the microbubble ("coupled" into the microbubble from a microfiber, prism, waveguide or the like). A material to be analyzed (liquid, gas or solid) is disposed within microbubble 10, where the WGMs will interact with the material being analyzed and modify the optical characteristics. The optical signal out-coupled from the microbubble will thus be altered and an optical receiver (not shown) used to characterize the material based upon the optical signal changes. When used as an optical laser, a propagating optical signal is again coupled into the microbubble to create circulating WGMs. An active lasing material is disposed within the microbubble and functions to efficiently amplify the circulating WGMs.

Figure 4:
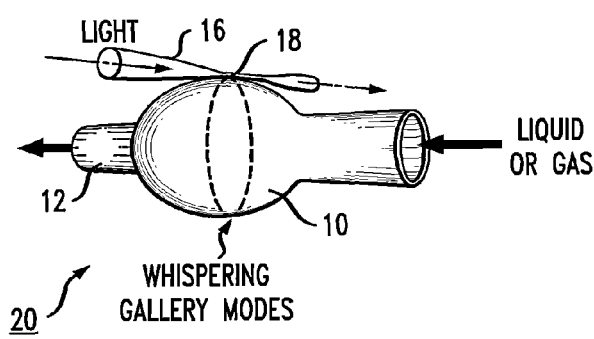
FIG. 4 illustrates an exemplary microbubble optical resonator of the present invention used with an optical microfiber in a sensing application.

FIG. 4 illustrates an exemplary optical sensor 20 utilizing microbubble 10 of FIG. 2 as a resonating device. As shown, a sample material (liquid or gas) is introduced into microcapillary 12 and flows therethrough. In this particular embodiment, input coupling of a "probing" optical signal is provided by an optical fiber taper 16 that is positioned with respect to microbubble 10 such a waist section 18 of optical fiber taper 16 contacts the outer surface of microbubble 10. In alternative embodiments, an optical prism, grating, waveguide or other suitable coupling device may be used to introduce the probing optical signal to microbubble 10.

Referring back to FIG. 4, the evanescent portion of the propagating optical signal will penetrate through the curved film forming the outer surface of microbubble 10 and begin to circulate as WGMs along the interior of microbubble 10. The circulating WGMs will interact with the sample material introduced to microcapillary 12. Advantageously, the geometry of microbubble 10 will confine the circulating WGMs to the central region of microbubble 10, forcing these modes to continue to circulate and create the desired high Q-factor cavity that will continuously interact with the sample material and create a high sensitivity optical output signal. The walls of microbubble 10 can be made extremely thin so as to increase the coupling efficiency between the optical fiber taper 16 (or prism or waveguide) and microbubble 10, further increasing the sensitivity of optical sensor 20. For example, an etchant such as HF may be introduced to microcapillary 12 and contacted with the inner walls of microbubble 10 for a predetermined period of time that is associated with etching away a desired thickness of the wall material.

Figure 5:
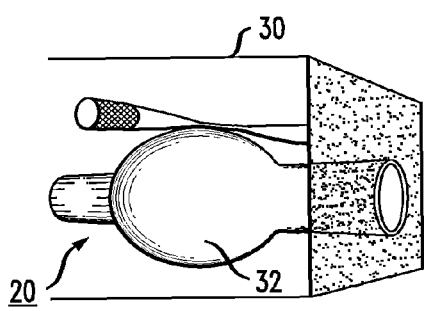
FIG. 5 is an alternative embodiment of the arrangement of FIG. 4, where the microbubble is immersed in a polymer matrix having a relatively low refractive index.

In a specific embodiment of the present invention, optical sensor 20 may be encapsulated in a polymer matrix of a low index material, providing additional rigidity to the final structure. FIG. 5 illustrates this embodiment of the present invention, where sensor 20 is surrounded by an encapsulant 30. Additionally, the capillary wall material within microbubble 10 (defined as interior region 32) may be completely or partially removed in this encapsulated embodiment (using an appropriate etchant, for example), allowing for the sample material (or active lasing material in the case of a laser embodiment) to be in direct contact with the low-index encapsulant. In this case, the optical signal propagating along optical fiber taper 16 is directly coupled to interior region 32. The encapsulation also results in creating an extremely robust device. A curable, low-index liquid polymer may be used as encapsulant 30. If the capillary material is entirely removed, the light propagating along optical fiber taper 16 will be directly coupled to interior region 32.

In optical filtering applications, the microbubble resonator of the present invention may be "tuned" by introducing a change to the physical properties of the microbubble. Specific types of "changes" that will provide tuning include, but are not limited to, mechanical deformation of the bubble, varying the temperature of the bubble, applying an electromagnetic field to the bubble, etc. These changes allow for improved wavelength sensitivity along the associated optical fiber taper, creating an optical filter suitable for many applications.

Figure 6:
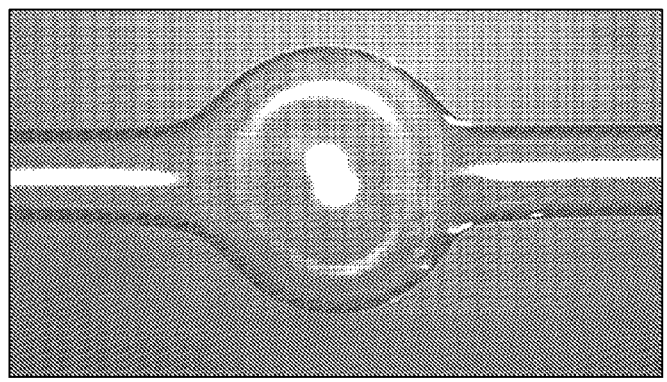
FIG. 6 is a rendition of an exemplary microbubble that has been formed in the laboratory.
Figure 7:
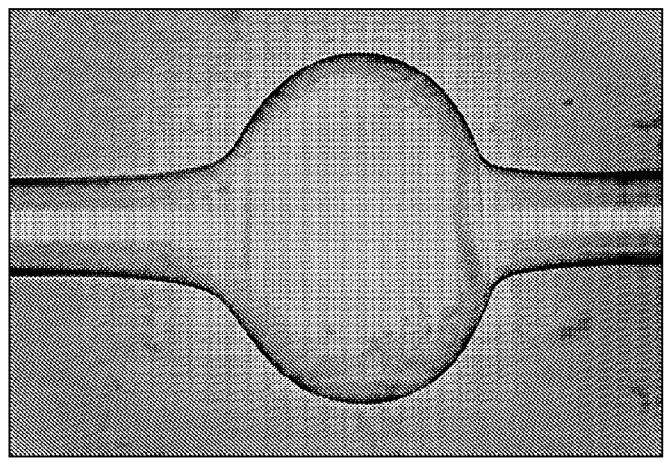
FIG. 7 shows an "elongated" microbubble that has been formed along a section of a microcapillary.
Figure 8:
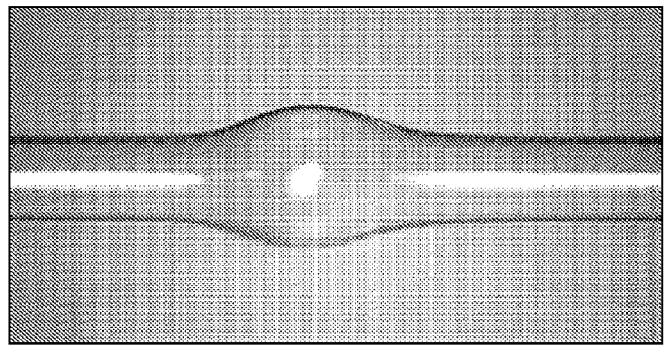
FIG. 8 shows a "squeezed" microbubble that has been formed along a section of a microcapillary.

It is to be understood that there is no need to form a perfectly spherical bubble along the microcapillary. As mentioned above, the microbubble may appear as an elongated 'bubble', or a squeezed 'bubble'. As long as a section of the microcapillary is modified such that a portion of its outer surface includes a curved film of optically transparent material, the confinement of the circulating WGMs will be improved, the Q factor of the resonator will be increased (with respect to the capillary-based LCORRS device) and the sensitivity of the resonator will be similarly increased. FIG. 6 is a rendition of an exemplary microbubble 100 that has been formed in the laboratory and found to provide the desired high-Q resonator. Another embodiment, illustrated an "elongated" microbubble is shown in FIG. 7, where FIG. 8 shows a "squeezed" microbubble. Each of these has been used in experimentations and found to sufficiently confine the circulating WGMs to create a high Q resonator.

It is also to be understood that the microbubble(s) of the present invention may be formed to comprise the entire extent of an associated microcapillary, or only a portion thereof. A further advantage of the microcapillary-based microbubble resonator of the present invention is the ability to directly splice the microbubble resonator to an optical fiber (at one termination, or both terminations of the associated microcapillary), providing relatively straightforward input/output ports for the delivery of a sample material, active laser material, etc. to the microbubble.

What is claimed is:

1. A method of fabricating an optical microbubble resonator, the method comprising the steps of:
   providing an optical microcapillary tube of an optically transparent material;
   heating a localized region of the optical microcapillary tube;
   modifying the air pressure within the heated, localized region; and
   deforming the localized region to create an outwardly-curving outer surface defining an optical microbubble for use as an optical microbubble resonator.

2. The method as defined in claim 1 wherein the air pressure is modified by blowing into the optical microcapillary tube.

3. The method as defined in claim 1 wherein the deforming step creates an essentially spherical microbubble.

4. The method as defined in claim 1 wherein the deforming step creates an elongated microbubble.

5. The method as defined in claim 1 wherein the deforming step creates a squeezed microbubble.

6. The method as defined in claim 1 wherein the method further comprises the step of:
   encapsulating the microcapillary tube and the microbubble within a low-index encapsulant material.

7. The method as defined in claim 6 wherein the method further comprises the step of: removing at least a portion of the microcapillary tube in the area of the microbubble, creating a cavity region defined by the low-index encapsulant material.

8. The method as defined in claim 7 wherein the material is removed by etching.

9. The method as defined in claim 1 wherein the method further comprises the step of splicing a section of optical fiber to the optical microcapillary tube.

* * * * *